United States Patent [19]

Crossman et al.

[11] Patent Number: 5,189,450
[45] Date of Patent: * Feb. 23, 1993

[54] HIGH MAGNIFICATION OPHTHALMIC LENS

[75] Inventors: Janet L. Crossman; Phillip J. Erickson, both of Bellevue; Gregory L. Heacock, Seattle, all of Wash.; Martin A. Mainster, Overland Park, Kans.

[73] Assignee: Ocular Instruments, Inc., Bellevue, Wash.

[*] Notice: The portion of the term of this patent subsequent to Apr. 16, 2008 has been disclaimed.

[21] Appl. No.: 703,680

[22] Filed: May 21, 1991

[51] Int. Cl.$^5$ .............................................. A61B 3/00
[52] U.S. Cl. ..................................................... 351/219
[58] Field of Search .................. 351/205, 219, 160 H, 351/160 R

[56] References Cited

U.S. PATENT DOCUMENTS

| 3,954,329 | 5/1976 | Pomerantzeff | 351/16 |
| 4,134,647 | 1/1979 | Ramos-Caldera | 351/6 |
| 4,410,245 | 1/1983 | Koester | 351/219 |
| 4,452,514 | 6/1984 | Spitznas | 351/206 |
| 4,469,413 | 9/1984 | Shirayanagi | 350/432 |
| 4,502,764 | 3/1985 | Riquin | 351/160 R |
| 4,627,694 | 12/1986 | Volk | 351/214 |
| 4,637,699 | 1/1987 | Sigelman | 351/205 |
| 4,669,839 | 6/1987 | Muchel | 351/221 |
| 4,671,631 | 6/1987 | Sigelman | 351/205 |
| 4,682,866 | 7/1987 | Volk | 351/205 |
| 4,704,018 | 11/1987 | Takhashi | 351/206 |
| 4,721,378 | 1/1988 | Volk | 351/205 |
| 4,728,183 | 3/1988 | Heacock et al. | 351/219 |
| 4,738,521 | 4/1988 | Volk | 351/205 |

FOREIGN PATENT DOCUMENTS

| 124502 | 5/1984 | European Pat. Off. | 351/219 |
| 2246182 | 3/1974 | Fed. Rep. of Germany | 351/219 |
| 2660505C2 | 9/1977 | Fed. Rep. of Germany | 351/219 |
| 2248814 | 5/1975 | France | 351/219 |
| 8805878 | 3/1988 | United Kingdom . | |

OTHER PUBLICATIONS

P. Roussel et al., "Contact Glass for Use . . . Optical Aspects," *International Ophthalmology* 6:183–190 (1983).

*Primary Examiner*—Rodney B. Bovernick
*Attorney, Agent, or Firm*—Christensen, O'Connor, Johnson & Kindness

[57] ABSTRACT

An ophthalmic lens which has three elements, a contact lens, a center lens, and an entry lens. The lens produces a magnified aerial image of the fundus of the eye. The lens is particularly useful because it provides high magnification and detail of the fundus as well as good stereoscopic field.

10 Claims, 1 Drawing Sheet

HIGH MAGNIFICATION OPHTHALMIC LENS

TECHNICAL BACKGROUND

The present invention relates to ophthalmic lenses employed in connection with ophthalmic diagnostic and surgical procedures and, more particularly, to a compound ophthalmic lens that is utilized for observation and magnification of the fundus and for delivery of laser energy thereto.

Ophthalmic lenses are conventionally used for observation of various locations within the eye by ophthalmologists. These ophthalmic lenses normally include a contact lens, that is, a lens that directly contacts the cornea of the eye, and may include an entry lens that is spaced in the anterior direction from the contact lens. The two lenses are normally joined by a housing.

Most ophthalmic lenses of the type just described have been created and designed for use as an observation tool utilized in conjunction with a slit lamp or ophthalmic microscope. While most prior lenses function reasonably well for use as an observation tool, the advent of laser microsurgery and the accompanying need to deliver a laser beam safely within the eye has created a need for ophthalmic lenses that not only provide improved images of the desired location in the eye but also have the capability to deliver laser energy to the desired location with minimum effect on other portions of the eye. One example of a modern ophthalmic lens utilized in diagnosis and surgical procedures is disclosed in U.S. Pat. No. 4,728,183. That lens uses an aspheric entry lens to produce an aerial image spaced from and anterior of the entry lens. A combination of the contact lens and the aspheric lens produces an aerial image that has very high resolution, even in the peripheral area of the image. The lens also produces very little reflected or scattered light as well as a nondistorting path through which the laser beam can pass during treatment of a patient's pathology. The lens disclosed in this patent also maintains a wide cone angle on the laser beam as it passes through the patient's cornea and crystalline lens to minimize energy absorption in those areas of the patient's eye. This lens, however, has a relatively small field of view on the order of ±45°. A second contact lens currently in use and disclosed in U.S. Pat. No. 5,007,729 supplements that disclosed in the '183 patent. That lens has a relatively wide field of view on the order of ±61°. This lens is especially useful for treatment of retinal detachment in the peripheral area of the fundus and also for other procedures such as panretinal photocoagulation.

Both of these prior art lenses, however, have magnifications less than 1X. The '183 lens has a magnification on the order of 0.96, while the lens disclosed in the '729 patent has a magnification on the order of 0.66. It is desirable to possess a magnifying lens that provides superior retinal clarity for detecting macular problems such as macular degeneration and diabetic retinal thickening. A magnifying lens will also facilitate the location of subtle vascular landmarks during macular photocoagulation. These fine details may be apparent angiographically but are hard to find without high magnification in the low contrast ophthalmoscopic image. It is preferable to maintain an aerial image that is flat or concave when viewed from the anterior direction, that is, concave as viewed by the ophthalmologist, since an image that is convex toward the ophthalmologist tends to be unacceptably distorted, and also degrades stereo perception. Moreover, it is preferable to maintain the aerial image less than about 45 millimeters from the patient's cornea so that the lens is useful with all standard slit lamp microscopes used by ophthalmologists. In addition, while achieving these desirable ends, it is also desirable to provide a lens that has a relatively wide binocular and stereoscopic field of view.

SUMMARY OF THE INVENTION

The present invention provides an improved ophthalmic lens that provides a higher magnification while providing an aerial image that is flat or slightly concave when viewed from the anterior direction and maintaining the aerial image close enough to the eye so that it can be used with current slit lamp microscopes, as well as other types of microscopes. In addition, the contact lens of the present invention provides an excellent field of view while maintaining a high degree of stereoscopic field. The lens constructed in accordance with the present invention comprises a contact lens having a posterior surface and an anterior surface. The posterior surface of the lens has a curvature compatible with the anterior surface of a cornea. The anterior surface of the contact lens has a predetermined radius of curvature $R_{2C}$. The indices of refraction of the contact lens can range from 1.40 to 1.95. $R_{2C}$ can range from 7.0 mm to 22.4 mm, and the axial thickness of the contact lens ($T_C$) can range from 0.5 mm to 4.5 mm. The ophthalmic lens also has an entry lens positioned anterior to the contact lens. The entry lens is aspheric, with its surfaces being defined by the formula:

$$Z = \frac{CK^2}{1 + \sqrt{1 - C^2 E K^2}},$$

wherein $C = (1/R)$, $E = b + 1$, and $K^2 = x^2 + y^2$, wherein for the anterior surface of the lens, $R_{2EL}$ ranges from 18.4 mm to 35.3 mm and $b_{2EL}$ ranges from 0 to $-40$, and wherein the posterior surface of said lens, $R_{1EL}$ ranges from 13.3 mm to 20.7 mm, and $b_{1EL}$ ranges from 0 to $-10$. The entry lens preferably has a thickness ($T_{EL}$) ranging from 1.0 mm to 32.1 mm. Finally, the ophthalmic lens constructed in accordance with the present invention includes a center lens positioned between the contact lens and the entry lens. The optical axes of the contact lens, the center lens and the aspheric lens are substantially coincident. The center lens has a posterior surface having a radius of curvature $R_{1CL}$ and an anterior surface of the center lens having a radius of curvature $R_{2CL}$. The center lens element receives light rays emerging from the eye and the contact lens and refracts the light rays toward the optical axis of the ophthalmic lens. The entry lens collects the light rays emerging from the center lens and produces an aerial image anterior to and preferably in close proximity to the entry lens. The contact lens and the center lens element are positioned relative to each other and to the entry lens and have their radii of curvature chosen such that light rays originating on the fundus of the eye are magnified in the aerial image produced by the entry lens at a magnification greater than 1.0X. Indices of refraction for the center lens can range from 1.40 to 1.95. $R_{1CL}$ can range from $-32.8$ mm through infinity to 195.9 mm. $R_{2CL}$ can range from 23.9 mm to 66.1 mm, and the axial thickness of the center lens ($T_{CL}$) can range from 0.5 mm to 8.7 mm.

BRIEF DESCRIPTION OF THE DRAWINGS

A better understanding of the present invention can be derived by reading the ensuing specification in conjunction with the accompanying drawings wherein the FIGURE is a schematic view of the lens constructed in accordance with the present invention shown positioned on a patient's eye.

DETAILED DESCRIPTION OF THE INVENTION

Figure 1:
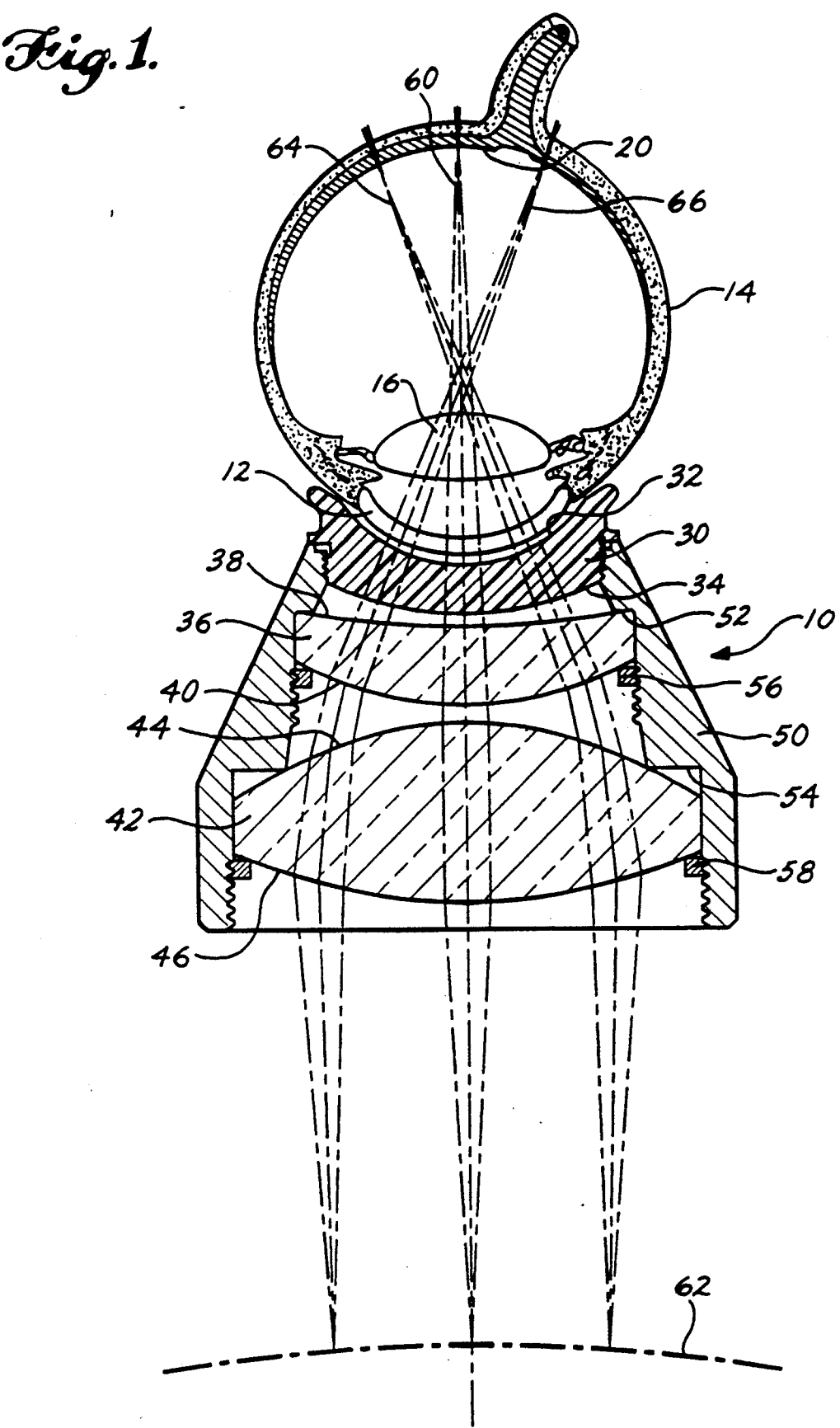

Referring first to the FIGURE, the ophthalmic lens 10 constructed in accordance with the present invention is positioned over the cornea 12 of a human eye, schematically represented at 14. The eye includes the crystalline lens 16 and the fundus 20.

The ophthalmic lens 10 includes a contact lens 30 having a posterior surface 32 and an anterior surface 34. The posterior surface of the contact lens has a radius $R_{1C}$ that is compatible with the cornea. While $R_{1C}$ may be the same radius as that of the average human cornea, it is preferred that $R_{1C}$ be slightly less than the radius of the anterior surface of the average human cornea. Preferably, the radius $R_{1C}$ is chosen so that slight vaulting occurs along the optical axis to separate the posterior surface of the contact lens from the optical region of the cornea. A preferred radius $R_{1C}$ is $-7.45$ mm. The thickness $T_C$ of the contact lens and the anterior radius $R_{2C}$ of the contact lens are chosen in accordance with the critical design parameters of the present invention discussed in more detail below.

A center lens 36 is positioned anterior to the contact lens. The posterior surface 38 of the lens has a radius $R_{1CL}$. The anterior surface 40 of the center lens has a radius $R_{2CL}$. Both the posterior radius $R_{1CL}$ and the anterior radius $R_{2CL}$, as well as the thickness $T_{CL}$ of the center lens, are also determined in accordance with the critical design parameters of the present invention, discussed in more detail below.

The entry lens 42 is an aspheric lens designed especially for the ophthalmic lens of the present invention. Both the posterior and anterior surfaces 44 and 46, respectively, of the aspheric lens are defined by the formula:

$$Z = \frac{CK^2}{1 + \sqrt{1 - C^2EK^2}},$$

wherein $C = (1/R)$, $E = b + 1$, and $K^2 = x^2 + y^2$. Higher order aspheric terms have been omitted from the equation because they have an insignificant effect on the optical performance of the lens system. Also manufacturing to the tolerances mandated by higher order terms is expensive.

For the posterior surface of the aspheric lens, $R_{1EL}$ can range from 13.3 mm to 20.7 mm and preferably is 15.94 mm $\pm 4\%$. For the posterior surface, $b_{1EL}$ can range from 0 to $-10$ and preferably is about $-2.00 \pm 10\%$. For the anterior surface of the lens, $R_{2EL}$ can range from 18.4 mm to 35.3 mm and preferably is about 23.53 mm $\pm 4\%$. For the anterior surface, $b_{2EL}$ can range from about 0 to $-40$ and preferably is about $-4.27 \pm 10\%$. The sign convention for the foregoing formula is that the Z axis extends from the vertex of the surface in the direction of the center of curvature of the lens surface, as defined by the vertex radius. The center thickness $T_{EL}$ of the aspheric lens along the optical axis can range from 1.0 mm to 32.1 mm, and is preferably 9.00 mm $\pm 4\%$. A most preferred diameter for the aspheric lens is about 23.00 $\pm 0.2$ mm.

The contact lens, center lens and aspheric entry lens can be made from any suitable optically transparent material such as polymethylmethacrylate (PMMA) or glass having an index of refraction from 1.40 to 1.95. In the preferred embodiment of the invention, the contact lens comprises PMMA or a similar suitable material having an index of refraction of about 1.492 $\pm 0.020$. In the preferred embodiment, the center lens is comprised of a transparent optical material, preferably glass, having an index of refraction most preferably of 1.517 $\pm 0.020$. The aspheric entry lens is comprised of a suitable optical material, preferably an allyl diglycol carbonate polymer, has an index of refraction most preferably 1.504 $\pm 0.020$. The three lenses are held by a lens holder 50 of conventional design. The holder positions the lenses about 0.5 mm apart. The circumference of the contact lens is externally threaded and engages an internally threaded bore at the posterior end of the cone, while the center lens and aspheric lens rest on shoulders 52 and 54 and are retained against those shoulders by conventional threaded retaining rings 56 and 58.

In use, light from the fundus in the region of the optical axis of the eye and the lens travels along a path indicated by light ray 60 through the crystalline lens 16, the cornea 12 and along the optical axis of the ophthalmic lens 10. The rays are focused in an aerial plane indicated by dot-dash line 62, anterior to the anterior surface of the entry lens 42. In accordance with the present invention, light rays from the adjacent portions of the fundus of the eye travel along paths indicated by ray tracing 64 and 66. The rays pass through the crystalline lens 16 and the cornea 12 and into the contact lens 30. The contact lens, designed in accordance with the present invention, refracts the rays toward the optical axis of the lens. The rays are then intercepted by the peripheral portions of the center lens which in turn refracts the rays again toward the optical axis of the lens. The rays 64 and 66 are then intercepted and refracted by the entry lenses and focused at the aerial image plane 62.

In accordance with the preferred embodiment of the invention, the aerial image is essentially flat. One of the obstacles that had to be surmounted in the design of the present lens is to maintain the aerial image which is flat or slightly concave when viewed from the anterior direction. As one of ordinary skill increases the dioptric power of the lenses in a lens combination of this sort, the aerial image tends to become convex in the anterior direction. A convex aerial image is undesirable because it causes the ophthalmologist to have a feeling of stereoscopic disorientation. It is preferred that the aerial image be positioned greater than about 2 mm but less than 30 mm from the anterior surface of the entry lens, and more preferably from 22 to 23 mm from the entry lens. The optics of the present lens are also designed so that the aerial image is less than 45 mm, and most preferably 40 mm, from the anterior surface of the cornea. These distances are measured using the average emmetropic human eye. In this manner, the ophthalmic lens can be used with virtually all of the conventional slit lamp microscopes in use by physicians.

The optics of the contact lens and center lens are designed in conjunction with the optics of the aspheric lens to achieve the objectives of the ophthalmic lens of the present invention. Use of aspherical surfaces for the contact and center lenses were considered, but found not necessary to achieve the objectives of the invention. The optical parameters of the contact lens, center lens and aspheric lens are, however, critical to provide the desired objectives, that is, an ophthalmic lens that magnifies the fundus, that retains an aerial image that is flat or slightly concave when viewed from the anterior direction, and provides a relatively wide field of view for a magnifying lens with a large stereoscopic field. Specifically, the lens 10 provides an aerial image having a magnification greater than 1.0×, preferably from 1.1× to 1.5×, and most preferably 1.25×±0.05×. In addition, the preferred lens also provides an instantaneous binocular field of view on the order of ±34° and a stereoscopic field on the order of ±14°, both measured from the optical axis using the posterior nodal point of the eye as the vertex of the angle. The optical parameters of the three lenses also combine to yield a lens that has an aerial image that is sufficiently close to the cornea so that the lens can be used with virtually all conventional slit lamp microscopes.

The lens parameters discovered by applicant are set forth in the table below. The set of values for which a workable combination of elements can be found are set forth in the preferred range of parameters. A second set of parameters are most preferred and encompass the preferred embodiment of the present invention.

| Lens | Preferred Parameters | Most Preferred Parameters |
|---|---|---|
| Contact lens | | |
| $R_{1C}$ | −6.5 to −8.4 | −7.45 ± 4% |
| $R_{2C}$ | 7.0 to 22.4 | 15.10 ± 4% |
| $T_C$ | 0.5 to 4.5 | 2.50 ± 4% |
| $N_C$ | 1.40 to 1.95 | 1.492 ± .02 |
| Center lens | | |
| $R_{1CL}$ | −32.8 through infinity to 195.9 | −90.00 ± 4% |
| $R_{2CL}$ | 23.9 to 66.1 | 33.72 ± 4% |
| $T_{CL}$ | 0.5 to 8.7 | 4.00 ± 4% |
| $N_{CL}$ | 1.40 to 1.95 | 1.517 ± .02 |
| Entry lens | | |
| $R_{1EL}$ | 13.3 to 20.7 | 15.94 ± 4% |
| $b_{1EL}$ | 0 to −10 | −2.00 ± 10% |
| $R_{2EL}$ | 18.4 to 35.3 | 23.53 ± 4% |
| $b_{2EL}$ | 0 to −40 | −4.27 ± 10% |
| $T_{EL}$ | 1.0 to 32.1 | 9.00 ± 4% |
| $N_{EL}$ | 1.40 to 1.95 | 1.504 ± 0.020 |

All dimensions are in millimeters. The indices of refraction are measured at a wavelength of 587 nanometers.

Also in the preferred embodiment, the respective diameters of the contact, center and entry lenses are 14.00±0.20 mm, 17.00±0.20 mm, and 23.00±0.20 mm, respectively. These three lenses should be spaced from each other by distances that provide optimum system performance. This spacing can range from 0 to 10 mm. In the preferred embodiment, it is desirable to position the three lenses as closely as possible to each other, but some actual separation must by necessity be present. Thus, it is preferred that the distance between each of the lenses is approximately 0.5 mm.

A lens constructed and designed in accordance with the parameters set forth above will achieve all of the functional characteristics above. The present invention has been disclosed in connection with a preferred embodiment. It is intended that one of ordinary skill will be able to effect various alterations, substitutions of equivalents and make other changes without departing from the broad concepts disclosed herein. It is therefore intended that the Letters Patent granted hereon be limited only by the definition contained in the appended claims and equivalents thereof.

The embodiments of the invention in which an exclusive property or privilege is claimed are defined as follows:

1. A magnifying ophthalmic lens for observing the fundus of the eye and for delivering laser energy thereto comprising:

a contact lens having a posterior surface and an anterior surface, said posterior surface having a curvature compatible with the anterior surface of a cornea, the anterior surface of the contact lens having a predetermined radius of curvature $R_{2C}$, wherein the indices of refraction of said contact lens can range from 1.40 to 1.95, $R_{2C}$ can range from 7.0 mm to 22.4 mm and the axial thickness of the contact lens ($T_C$) can range from 0.5 mm to 4.5 mm, an entry lens positioned anterior to the contact lens, the entry lens being aspheric, the surfaces of the entry lens being defined by the formula:

$$Z = \frac{CK^2}{1 + \sqrt{1 - C^2 E K^2}},$$

wherein
$C = (1/R)$,
$E = b + 1$, and
$K^2 = x^2 + y^2$,
wherein for the anterior surface of the lens,
$R_{2EL}$ ranges from 18.4 mm to 35.3 mm and
$b_{2EL}$ ranges from 0 to −40, and
wherein for the posterior surface of said lens,
$R_{1EL}$ ranges from 13.3 mm to 20.7 mm, and
$b_{1EL}$ ranges from 0 to −10,
said entry lens having a thickness ($T_{EL}$) ranging from 1.0 mm to 32.1 mm, wherein
said entry lens has an index of refraction ranging from 1.4 to 1.95, and
a center lens positioned between the contact lens and the entry lens, the optical axes of the contact lens, the center lens, and the aspheric lens being substantially coincident, the center lens having a posterior surface having a radius of curvature $R_{1CL}$, the anterior surface of the center lens having a radius of curvature $R_{2CL}$, the center lens element receiving light rays emerging from the eye and the contact lens and refracting the light rays toward the optical axis of the ophthalmic lens, the entry lens collecting the light rays emerging from the center lens and producing an aerial image anterior to the entry lens, the contact lens and the center lens element being positioned relative to each other and to the entry lens and having their radii of curvatures chosen such that light rays originating on the fundus of the eye are magnified in the aerial image produced by the entry lens, at a magnification greater than 1.0×, and wherein the indices of refraction for the center lens can range from 1.40 to 1.95, $R_{1CL}$ can range from −32.8 mm through infinity to 195.9 mm, $R_{2CL}$ can range from 23.9 mm to 66.1 mm and the axial thickness of the center lens ($T_{CL}$) can range from 0.5 mm to 8.7 mm.

2. The ophthalmic lens of claim 1, wherein said aerial image is flat or slightly concave when viewed from the anterior direction.

3. The ophthalmic lens of claim 1, wherein the contact lens comprises polymethylmethacrylate, and the center lens comprise glass and the entry lens comprises an allyl diglycol carbonate polymer.

4. The ophthalmic lens of claim 3, wherein the index of refraction of the center lens is $1.517 \pm 0.02$, $R_{1CL}$ is $-90.0$ mm$\pm 4\%$, $R_{2CL}$ is 33.72 mm$\pm 4\%$, $T_{CL}$ is 4.00 mm$\pm 4\%$, wherein said contact lens has a radius of curvature $R_{1C}$, and wherein the index of refraction of the contact lens is $1.492 \pm 0.02$, $R_{1C}$ is $-7.45$ mm$\pm 4\%$, $R_{2C}$ is 15.10 mm$\pm 4\%$, and $T_C$ is 2.50 mm$\pm 4\%$.

5. The ophthalmic lens of claim 4, wherein the index of refraction of the entry lens is $1.504 \pm 0.020$, and wherein $R_{1EL}$ is 15.94 mm$\pm 4\%$ and $R_{2EL}$ is 23.53 mm$\pm 4\%$, $b_{1EL}$ for the posterior surface is about $-2.00 \pm 10\%$ and $b_{2EL}$ for the anterior surface is about $-4.27 \pm 10\%$.

6. The ophthalmic lens of claim 1, wherein the aerial image is positioned greater than 2 mm and less than 30 mm from the anterior surface of the entry lens.

7. The ophthalmic lens of claim 5, wherein the aerial image is positioned from 22.0 mm to 23.0 mm from the anterior surface of the entry lens, as measured using the average emmetropic human eye.

8. The ophthalmic lens of claim 1, wherein the magnification is $1.25 \times \pm 0.05$.

9. A magnifying ophthalmic lens for observing the fundus of the eye and for delivering laser energy thereto comprising:
a contact lens having a posterior surface and an anterior surface, said posterior surface having a curvature compatible with the anterior surface of a cornea, the anterior surface of the contact lens having a predetermined curvature, wherein the indices of refraction of said contact lens can range from 1.40 to 1.95, and the axial thickness of the contact lens ($T_C$) can range from 0.5 mm to 4.5 mm,
an entry lens positioned anterior to the contact lens, the entry lens being aspheric, the surfaces of the entry lens being defined by the formula:

$$Z = \frac{CK^2}{1 + \sqrt{1 - C^2 E K^2}},$$

wherein
$C = (1/R)$,
$E = b + 1$, and
$K^2 = x^2 + y^2$,
wherein for the anterior surface of the lens,
$R_{2EL}$ ranges from 18.4 mm to 35.3 mm and $b_{2EL}$ ranges from 0 to $-40$, and
wherein for the posterior surface of said lens,
$R_{1EL}$ ranges from 13.3 mm to 20.7 mm, and $b_{1EL}$ ranges from 0 to $-10$,
said entry lens having a thickness ($T_{EL}$) ranging from 1.0 mm to 32.1 mm, wherein
said entry lens has an index of refraction ranging from 1.4 to 1.95, and
a center lens positioned between the contact lens and the entry lens, the optical axes of the contact lens, the center lens, and the aspheric lens being substantially coincident, the center lens having a posterior surface having a radius of curvature $R_{1CL}$, the anterior surface of the center lens having a radius of curvature $R_{2CL}$, the center lens element receiving light rays emerging from the eye and the contact lens and refracting the light rays oward the optical axis of the ophthalmic lens, the entry lens collecting the light rays emerging from the center lens and producing an aerial image anterior to the entry lens, the contact lens and the center lens element being positioned relative to each other and to the entry lens and having their curvatures chosen such that light rays originating on the fundus of the eye are magnified in the aerial image produced by the entry lens, at a magnification greater than $1.0 \times$, and wherein the indices of refraction for the center lens can range from 1.40 to 1.95, $R_{1CL}$ can range from $-32.8$ mm through infinity to 195.9 mm, $R_{2CL}$ can range from 23.9 mm to 66.1 mm and the axial thickness of the center lens ($T_{CL}$) can range from 0.5 mm to 8.7 mm.

10. An ophthalmic lens for viewing the fundus comprising:
(a) a contact lens having a posterior surface and an anterior surface, said posterior surface having a curvature compatible with the cornea and adapted to be positioned in juxtaposed contact therewith, a center lens, and an entry lens, said lenses being aligned along their respective optical axes, said lenses being constructed to gather light rays from the fundus and focus them in a magnified aerial image, said magnification being in the range of $1.1 \times$ to $1.5 \times$, said entry lens being positioned anterior to the contact lens, the entry lens being aspheric, the surfaces of the entry lens being defined by the formula:

$$Z = \frac{CK^2}{1 + \sqrt{1 - C^2 E K^2}},$$

wherein
$C = (1/R)$,
$E = b + 1$, and
$K^2 = x^2 + y^2$,
wherein for the anterior surface of the lens,
$R_{2EL}$ ranges from 18.4 mm to 35.3 mm and $b_{2EL}$ ranges from 0 to $-40$, and
wherein for the posterior surface of said lens,
$R_{1EL}$ ranges from 13.3 mm to 20.7 mm, and $b_{1EL}$ ranges from 0 to $-10$,
said entry lens having a thickness ($T_{EL}$) ranging from 1.0 mm to 32.1 mm, wherein
said entry lens has an index of refraction ranging from 1.4 to 1.95.

* * * * *